United States Patent

Morishige et al.

[11] Patent Number: 5,818,576
[45] Date of Patent: Oct. 6, 1998

[54] EXTRANEOUS SUBSTANCE INSPECTION APPARATUS FOR PATTERNED WAFER

[75] Inventors: Yoshio Morishige; Hisato Nakamura; Tetsuya Watanabe, all of Saitama, Japan

[73] Assignee: Hitachi Electronics Engineering Co., Ltd., Tokyo, Japan

[21] Appl. No.: 744,454

[22] Filed: Nov. 7, 1996

[30] Foreign Application Priority Data

Nov. 28, 1995 [JP] Japan ................................ 7-332622

[51] Int. Cl.$^6$ .................................................. G01N 21/89
[52] U.S. Cl. .................................... 356/237; 250/559.45
[58] Field of Search .................................. 356/237, 394, 356/430, 448, 239, 338, 431, 429, 426, 446; 250/562, 563, 572, 208.1, 599.45–599.49, 548; 382/8, 25, 26; 358/106, 101, 107, 212, 214, 216, 406, 474, 482, 483, 498, 75

[56] References Cited

U.S. PATENT DOCUMENTS

| 4,795,911 | 1/1989 | Kohno et al. ............................ 250/572 |
| 4,799,175 | 1/1989 | Sano et al. .............................. 364/552 |
| 5,144,132 | 9/1992 | Kitakado ................................. 250/208 |
| 5,146,509 | 9/1992 | Hara et al. ................................. 382/8 |
| 5,153,444 | 10/1992 | Maeda et al. ........................... 250/562 |
| 5,463,459 | 10/1995 | Morioka et al. ........................ 356/237 |
| 5,471,066 | 11/1995 | Hagiwara ................................ 250/559 |
| 5,644,393 | 7/1997 | Nakamura et al. ..................... 356/237 |

*Primary Examiner*—Frank G. Font
*Assistant Examiner*—Michael P. Stafira
*Attorney, Agent, or Firm*—Fay, Sharpe, Beall, Fagan, Minnich & McKee

[57] ABSTRACT

An extraneous substance inspection apparatus for a patterned wafer, according to the present invention, comprises an optical sensor having a plurality of detecting portions arranged to receive the scattering light corresponding to pixels and produce the detection signal corresponding to the respective pixels, a delay circuit responsive to the detection signal from the optical sensor for delaying the detection signal by a predetermined time and a judging circuit for judging an absence or presence of contaminant by comparing an output of the delay circuit with the detection signal from said optical sensor, wherein the wafer is inclined by a predetermined angle with respect to a direction parallel to the arranging direction of the detecting portions of the optical sensor and the predetermined time corresponds to a difference in scan time between a position of one pixel and substantially the same position as that of the one pixel in one chip of another pixel in another chip adjacent to that chip, the another pixel being determined corresponding to the predetermined angle in the X-Y scanning.

9 Claims, 3 Drawing Sheets

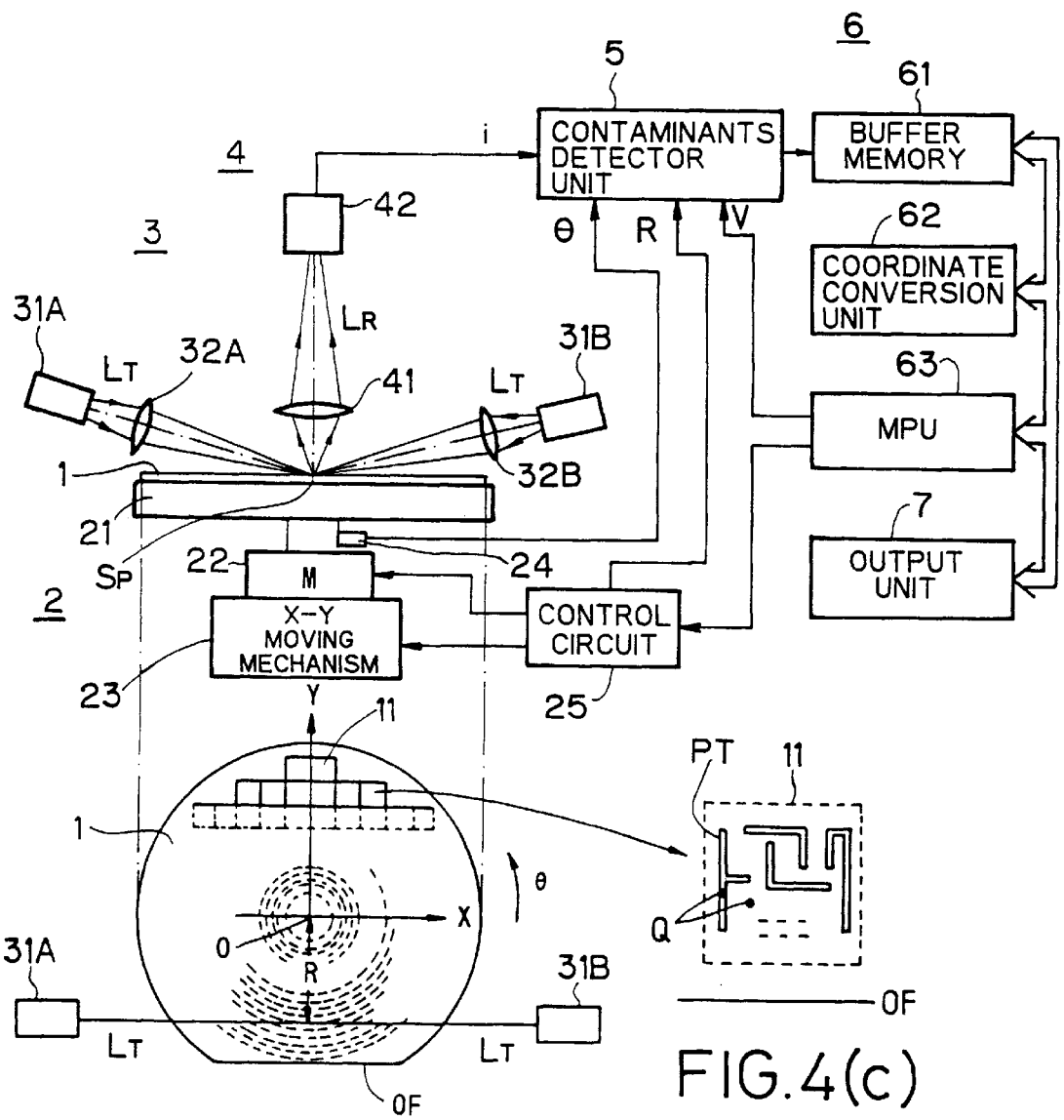

EXTRANEOUS SUBSTANCE INSPECTION APPARATUS FOR PATTERNED WAFER

FIELD OF THE INVENTION

The present invention relates to an extraneous substance inspection apparatus for a patterned wafer and, particularly, to a extraneous substance inspection apparatus of an X-Y scanning type which can detect extraneous substance or contaminants on a patterned wafer with improved preciseness.

BACKGROUND OF THE INVENTION

In a manufacturing process for integrated circuits (IC's), extraneous substance or contaminants on a surface of a wafer having various patterns of semiconductor regions, insulating regions, electrodes and wiring causes performance of resulting IC's to be degraded. In order to avoid such degradation of performance of the IC, contaminants of the wafer are detected in forming each of the various patterns by a wafer contaminant inspection apparatus.

There are two types of wafer contaminant inspection apparatus, one being X-Y scan type in which a surface of a wafer is scanned with laser beams in X and Y directions and the other being rotary scan type in which a surface of wafer is scanned spirally or concentrically with a laser beam while the wafer is rotated.

FIG. 4(a) shows an example of construction of the wafer contaminants inspection apparatus of the rotary scan type. In FIG. 4(a), a patterned wafer 1 including IC chips 11 each containing a number of patterns is fixed onto a table 21 of a rotary mechanism 2. A surface of the wafer 1 is irradiated with laser beams $L_T$ from oppositely arranged laser sources 31A and 31B of a projector unit 3 at small angles of depression in the X directions. The laser beams are focused as spots $S_P$ by condenser lenses 32A and 32B, respectively, to define a contaminant detection area on the wafer 1. The wafer 1 is rotated in a $\Theta$ direction by a motor (M) 22 under a control of a control circuit 25 as shown in FIG. 4(b). The wafer 1 is further moved continuously or in step in the Y direction by an X-Y moving mechanism 23. As a result, the surface of the wafer 1 is scanned spirally or concentrically by the spots $S_P$.

By scanning with spots $S_P$, any contaminants adhering to the surface of the wafer 1 and/or to the patterns thereof produce scattering light $L_R$ which is collected by a collector lens 41 of a light receiving unit 4 and received by a light receiving portion 42 including, for example, CCD image sensors and amplifiers. The light receiving portion 42 outputs a luminance signal i indicating a luminance of the scattering light $L_R$ as a detection signal.

On the other hand, a rotary encoder 24 connected directly to the motor 22 of the rotary mechanism 2 generates an angle signal $\Theta$ indicating an angle of rotation of the wafer 1 and a position signal R indicating a scanning position of the spots $S_P$ moved in the Y direction, respectively, under a control of a control circuit 25 and these signals are supplied to a contaminant detector unit 5 together with the luminance signal i, as shown in FIG. 4(b).

The contaminant detector unit 5 preliminarily has a suitable threshold value V given by a microprocessor (MPU) 63 of a data processor unit 6. The luminance signal i input to the contaminant detector unit 5 is compared with the threshold value V to detect contaminants. A detection signal (data) of contaminants together with data of the rotation angle $\Theta$ of the wafer 1 and the scanning position signal R becomes a contaminant data which is transferred to and stored in a buffer memory 61 of the data processor unit 6 temporarily.

After the detection of contaminants over the whole surface of the wafer 1 is completed, coordinates of respective contaminant data stored in the buffer memory are converted from R$\Theta$ coordinates into X-Y coordinates by a coordinate conversion unit 62 and displayed as a map on an output unit 7 constructed with a CRT display, etc.

A pattern PT of wiring formed on the chip 11 is formed in a direction parallel to and/or perpendicular to an orientation flat (OF) of the wafer 1, as shown in FIG. 4(c). On the other hand, contaminants Q are randomly scattered on the pattern PT and other areas of the wafer surface which have no pattern. Scattered light $L_R$ from the pattern PT and the contaminants Q have features respectively. That is, the contaminants Q produce substantially omni-directional scattering light having magnitude corresponding to the size thereof. On the contrary, scattering light from an edge portion E of the pattern PT is rather stronger than that from an area portion of the pattern and has a directivity depending upon the direction of the pattern PT. This fact is shown in FIG. 5. In FIG. 5, the scattering light from the pattern PT is concentrated in hatched areas centered along lines making an angle $\Theta_P$ of about 22.5 degree with respect to X axis and Y axis.

Next, a construction of the contaminant inspection apparatus of the X-Y scan type will be described. The contaminant inspection apparatus of the X-Y scan type is constructed with substantially the same components as those shown in FIG. 4. Differences of the contaminant inspection apparatus of the X-Y scan type from that of the rotary scan type will be described. In the X-Y scan type apparatus, the motor 22 shown in FIG. 4 which is the rotary mechanism for the wafer 1 is used for merely positioning the wafer such that the orientation flat thereof becomes in parallel to the X or Y axis. The X-Y scan is performed by the X-Y moving mechanism 23. A laser beam $L_T$ from one of the laser light sources 31A and 31B of the projector unit 3 is usually used. Further, instead of the angle signal $\Theta$ and the position signal R, X and Y coordinates are sent from the control circuit 25 or the MPU 63 to the contaminants detection unit 5. The coordinate conversion unit 62 is removed.

In the contaminants inspection apparatus of the X-Y scan type, the control circuit 25 drives the motor 22 to position the orientation flat of the wafer 1 and then performs the X-Y scan by driving the X-Y moving mechanism 23 to detect contaminants at respective scanning points.

In the contaminant inspection apparatus of this type, the scattering light from the wafer is usually detected by the detection optical unit provided vertically. However, in order to improve the accuracy of contaminants detection, it is a recent tendency that the irradiating angle of laser beam to the pattern formed on the wafer when projected on the wafer surface is made about 45° and the scattering light from the pattern is received, so that an amount of scattering light reflected vertically of the pattern is reduced, resulting in the improved contaminant detection accuracy.

Incidentally, compared with the rotary scan system, the X-Y scan system has an advantage in that a position of contaminant can be detected precisely. However, the detection efficiency of the X-Y scan system is lower than that of the rotary scan system. In order to improve the detection efficiency of the X-Y scan system, it has been proposed to collimate a laser beam $L_T$ from the projector unit 3 to a line to form a line shaped contaminant detection area on the wafer, to focus an image of the line shaped contaminant detection area on a one dimensional CCD image sensor of the light receiving portion 42 and to detect the contaminant by an X-Y scanning. U.S. Pat. No. 5,644,393 entitled "Extraneous Substance Inspection Method and Apparatus" based on this system and assigned to the same assignee of this application isued on Jul. 1, 1997.

Further, in order to improve the accuracy of contaminant detection, the present inventors have proposed a technique in which contaminants are detected by comparing a contaminant detection value detected at a position of one chip with that at substantially the same position of a chip adjacent to the one chip. A U.S. patent application based on this technique is filed on the same day as the day of this application under the title of invention "Extraneous Substance Inspection Apparatus for Patterned Wafer", which is assigned to the same assignee of this application.

In a case where contaminants are detected by comparing a contaminant detection value detected at a position of one chip with that at substantially the same position of a chip adjacent to the one chip as in the above mentioned technique, it is necessary to arrange the line sensor of the light receiving optical system in parallel to or perpendicular to the wafer (pattern formed on the wafer) since detection values must be obtained from respective pixels. On the other hand, in order to perform a more accurate contaminant detection, it is preferable to reduce the amount of scattering light from the pattern by irradiating it with a laser beam inclined with respect to the wafer. In the case where contaminants are detected by comparing a contaminant detection value detected at a position of one chip with that at substantially the same position of a chip adjacent to the one chip, however, it is difficult to incline the projection optical system in such a way that laser beam is inclined while making the contaminant detection area parallel or perpendicular to the wafer.

SUMMARY OF THE INVENTION

An object of the present invention is to provide a contaminant inspection apparatus of X-Y scan type for detecting contaminants on a patterned wafer, which is capable of detecting contaminants accurately with improved throughput of contaminant detection.

In order to achieve the above object, the contaminant inspection apparatus for a patterned wafer according to the present invention, which detects contaminants on the patterned wafer having a pattern formed as IC chips on the basis of a signal which is obtained by irradiating the pattered wafer with laser beam at a predetermined angle with respect to a surface of the patterned wafer to scan the wafer in X and Y directions and receiving scattering light reflected from the patterned wafer to obtain a detection signal corresponding to an intensity of the received light, comprises an optical sensor having a plurality of detecting portions arranged to receive the scattering light correspondingly to pixels and produce the detection signal correspondingly to the respective pixels; a delay circuit responsive to the detection signal from the optical sensor for delaying the detection signal by a predetermined time and a judging circuit for judging an absence or presence of contaminant by comparing an output of the delay circuit with the detection signal from the optical sensor, wherein the wafer is inclined by a predetermined angle with respect to a direction parallel to the arranging direction of the detecting portions of the optical sensor and the predetermined time corresponds to a difference in scan time between a position of one pixel in one chip and substantially the same position as that of the one pixel of another pixel in another chip adjacent to that chip, the another pixel being determined correspondingly to the predetermined angle in the X-Y scanning.

In this manner, in the present invention, the optical sensor having the detecting portions arranged to detect detection signals (luminance signals) corresponding to respective pixels and the wafer is tilted with respect to the arranging direction of the detecting portions of the optical sensor. With this construction, the pattern formed on the wafer is also tilted and thus the amount of scattering light perpendicularly of the pattern is reduced, allowing contaminant detection to be performed correspondingly to respective pixels at high accuracy.

In this case, it becomes unnecessary to tilt the projecting optical system as well as the light receiving optical system similarly to the conventional system. Further, since the detection signal (luminance signal) obtained from a pixel through the light receiving optical system is delayed by a difference in scan time between the pixel in one chip and a pixel in another chip adjacent to that chip and compared with that obtained from the latter pixel in the corresponding position which is determined according to the inclination of the optical sensor, the contaminant detection can be performed in the similar manner to the detection in which adjacent chips are compared without inclination of the optical sensor.

As a result, it is possible to perform a contaminant detection of a patterned wafer efficiently with high precision by using the X-Y scanning.

According to another aspect of the present invention, the contaminants inspection apparatus for patterned wafer further comprises a level conversion circuit for converting a level of a detection signal obtained from one chip through the optical sensor into one of multi-valued levels. The delay circuit delays the level-converted detection signal and supplies the delayed signal to the judging circuit which judges a presence or absence of contaminant by comparing the delayed signal with a level-converted signal obtained from an adjacent chip in the similar manner.

In the present invention, a level of a detection signal, that is, luminance signal, obtained at a position on one IC chip is converted into one of a plurality of predetermined multi-valued levels and the one level is compared with a similarly converted level of a detection signal obtained at a similar position on another IC chip adjacent to the one IC chip. In this manner, the level of a reference value is not fixed and can be obtained from the adjacent IC chip. That is, in the present invention, the threshold value for contaminant detection is dynamically changed correspondingly to the light receiving condition and the inspecting condition. Further, since there are a plurality of conversion levels and the luminance signal obtained from the IC chip under inspection and the luminance signal obtained from the adjacent IC chip as the reference in comparison are varied similarly even if the conversion values are changed according to change of the light receiving condition and the inspecting condition, there is substantially no relative variation of the conversion values as the condition of comparison.

The level conversion to one of the multi-valued levels may be performed for the analog detection signal (referred to as "luminance signal", hereinafter) or for a digital value obtained by A/D conversion of the luminance signal. In the following description, the level conversion is performed for the digital signal.

When an object to be inspected is a pattern, there is a large scattering light produced and the level of the luminance signal becomes large correspondingly. Since, in this invention, the reference value for comparison is obtained from the adjacent IC chip, the position from which the luminance signal is obtained is different and there may be a case where only a small reference value for comparison can be obtained. In such case, a pattern from which a luminance signal having a high level compared with the level of a luminance signal on the reference side is obtained shall be detected as contaminant.

In order to avoid such situation, in an embodiment of the present invention, a first, pattern side level conversion circuit and a second, contamination side level conversion circuit are provided instead of a single level conversion circuit. A first level of a first luminance signal for detecting contaminants is obtained by converting a level of the first luminance signal obtained from a position in a certain one of IC chips, which is under inspection, by the first level conversion circuit and a second level of a second luminance signal is obtained by converting a level of the second luminance signal obtained from a position in another IC chip adjacent to the one IC chip, which corresponds to the position of the IC chip under inspection. The first level is compared with the second level. In this case, in order to avoid such erroneous detection of the pattern portion as contaminants, the first level conversion circuit performs a compression conversion such that a value of the converted level of the first luminance signal corresponding to a pattern portion of the one IC chip becomes smaller than a value of the converted level of the second luminance signal corresponding to a pattern portion of the adjacent IC chip. The compression conversion will be described in detail later on.

In the embodiment of the present invention, each of the first and second level conversion circuits converts a level of a signal into one of predetermined 8 (eight) steps. A width of each step of the first level conversion circuit is set as large as about 4 times a width of a corresponding step of the second level conversion circuit, so that the level conversion of the luminance signal in the first level conversion circuit is compressed to ¼.

When a single level conversion circuit is to be used, the single level conversion circuit converts levels of luminance signals obtained from corresponding positions of a detection side IC chip and a reference side IC chip into ones of predetermined steps, respectively, and the converted levels are compared with each other. In this case, the influence of variation of detecting condition is reduced compared with the conventional apparatus.

The number of levels set in the level conversion circuit is preferably 3 or more.

As mentioned previously, the first level conversion circuit is adapted to produce the level-converted reference level which is used as a comparison reference for detecting contaminants and is referred to as the pattern side level conversion circuit for the reason that patterns are formed on a major portion of the wafer surface and, in the X-Y scan system, a major portion of signals indicative of converted levels produced by this circuit are luminance signals obtained by the patterns. In this regard, the contaminant side level conversion circuit produces a signal indicative of a converted level of a luminance signal.

In the embodiment, the sensor for generating the luminance signal is composed of a row of a number of light receiving elements and a row of a corresponding number of CCD's arranged oppositely to the respective detecting elements. However, any optical sensor can be used instead of the row of CCD's so long as it can generate luminance signals correspondingly to a number of pixels as detection signals.

BRIEF DESCRIPTION OF THE DRAWINGS

FIG. 4(a) shows an example of a contaminant inspection apparatus of the rotary scan type;

FIG. 4(b) shows a relation between IC chips formed on a wafer and a scanning in the apparatus shown in FIG. 1; and FIG. 4(c) shows a relation between a pattern and contaminants on one of the IC chips shown in FIG. 4(b);

DETAILED DESCRIPTION OF THE PREFERRED EMBODIMENTS

Figure 1:
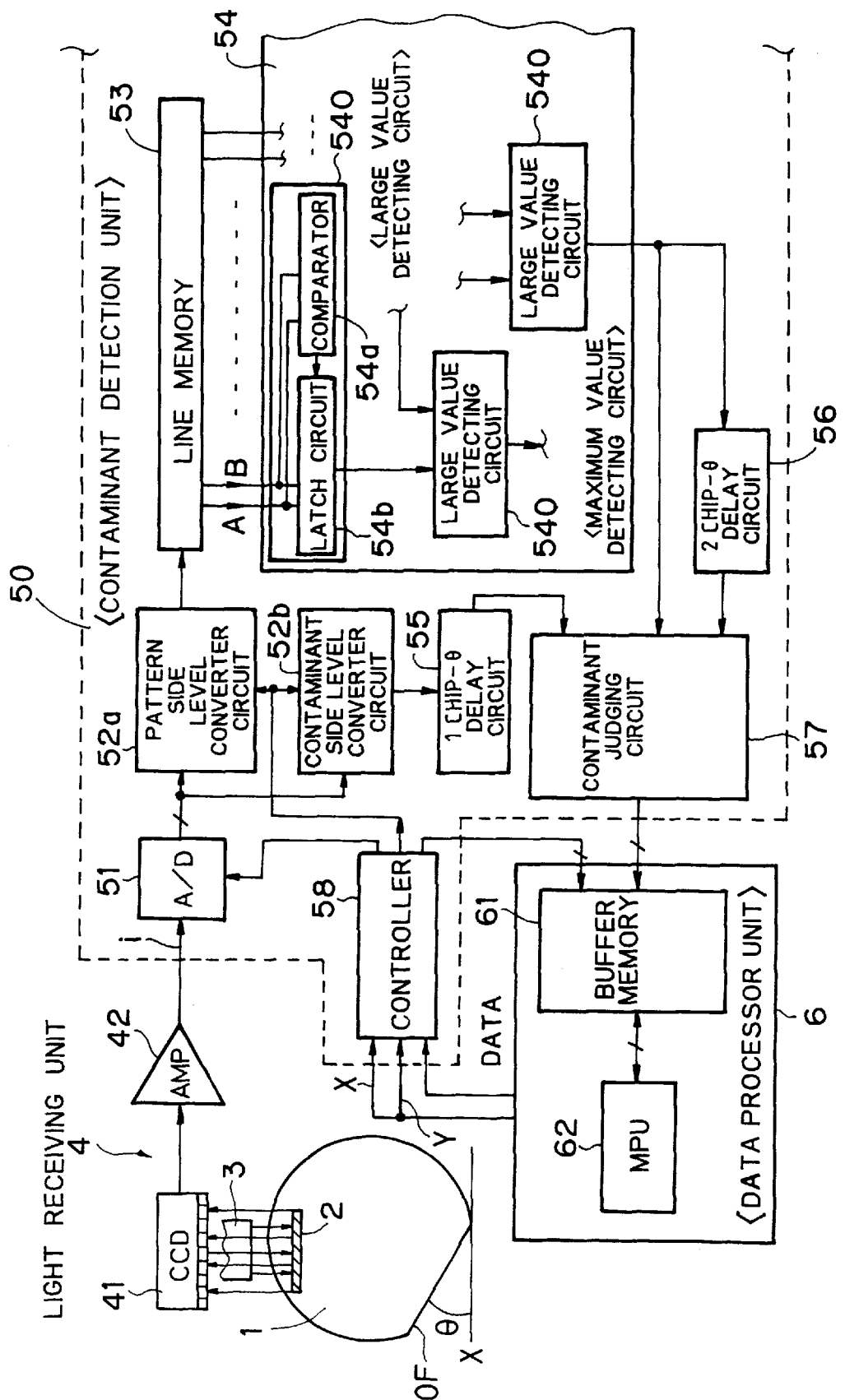
FIG. 1 is a block circuit diagram of a contaminant detecting unit of a contaminant inspection apparatus for patterned wafer, according to an embodiment of the present invention.

FIG. 1 shows a wafer 1 tilted clockwise with respect to an X axis which is a main scanning direction by an angle $\Theta$ in a range, for example, from 20 degrees to 45 degrees and mounted on an X-Y moving table of a contaminant inspection apparatus shown in FIG. 4. OF indicates an orientation flat of the wafer 1. A light projecting unit 3 of the contaminant inspection apparatus shown in FIG. 4 forms a striped contaminant detection area 2 on the wafer 1 in scanning the latter in X and Y directions.

A light receiving unit 4 of the apparatus shown in FIG. 4 is composed of, in this embodiment, a CCD image sensor 41 and an amplifier 42. The light projecting unit 3 and the CCD image sensor 41 of the light receiving unit 4 are arranged in parallel to the X axis. Therefore, a plurality of detection elements of the CCD image sensor 41 which are provided corresponding to respective pixels are arranged in a direction making an angle $\Theta$ with respect to the wafer 1.

Figure 2:
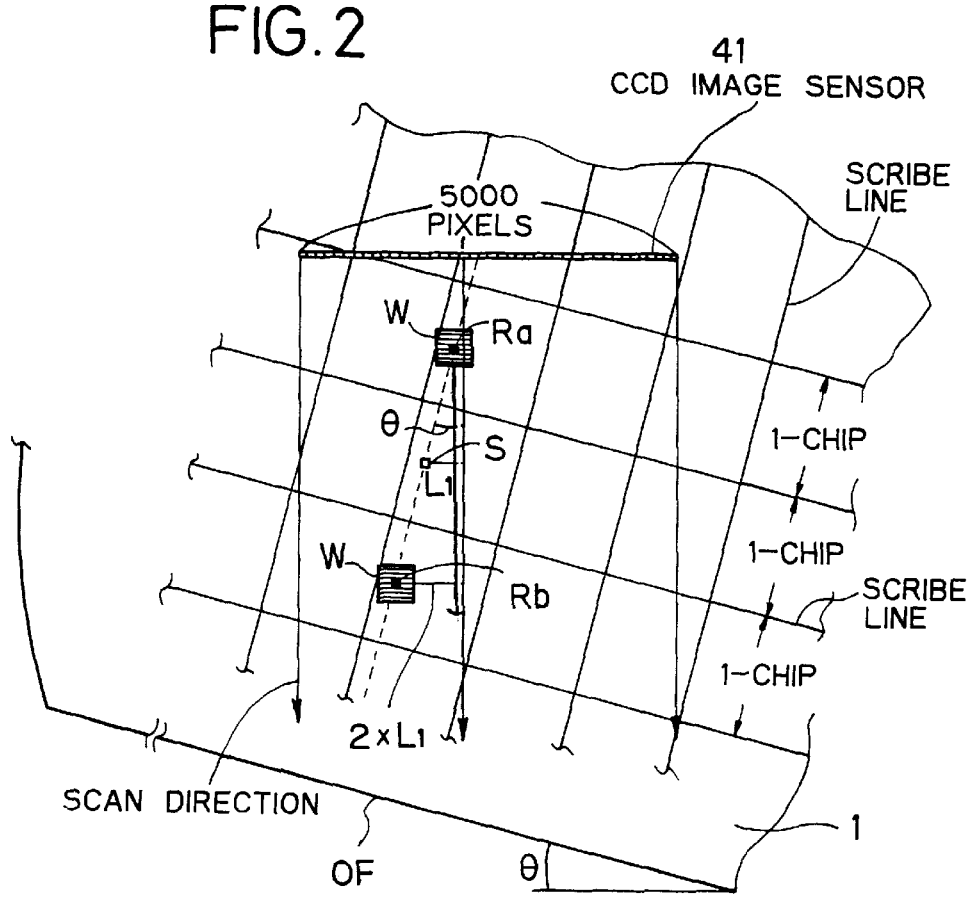
FIG. 2 is an illustration showing a detecting operation of the apparatus of FIG. 1.

As shown in FIG. 2, the wafer 1 has a number of chips as a pattern and the light projecting unit 3 emits a laser beam to a surface of the wafer 1 with a predetermined angle with respect thereto to scan it in X and Y directions. A scattering light reflected from the wafer 1 is received by the CCD image sensor 41 and a luminance signal output from the CCD image sensor 41 is amplified by the amplifier 42. A resultant luminance signal i from the amplifier 42 is sent to a contaminant detecting unit 50.

The contaminant detecting unit 50 corresponds to the contaminant detecting unit 4 shown in FIG. 4. The contaminant detecting unit 50 comprises an A/D converter circuit 51, a level converter circuit (referred to as "pattern side level converter circuit", hereinafter) 52a for obtaining a reference level for comparison by level-converting a luminance signal obtained from a pattern, a level conversion circuit (referred to as "contaminant side level converter circuit", hereinafter) 52b for level-converting a luminance signal obtained from contaminants, a line memory 53, a maximum value detector circuit 54, a 1 chip–$\Theta$ delay circuit 55, a 2 chips–$\Theta$ delay circuit 56, a contaminant judging circuit 57 and a controller 58.

In this embodiment, a laser beam $L_T$ from a light projector unit 3 is collimated to a line and defines a contaminant detection area on a wafer and an image of the line shaped contaminant detection area is focused on a line of CCD image sensors 42a of a light receiving unit 42 to detect contaminants by an X-Y scanning thereof, as shown in FIGS. 1 and 2. In this embodiment, the line of CCD image sensors 42a is long enough to cover about 5000 pixels. The coordinates conversion unit 62 shown in FIG. 4 is removed since the apparatus is of X-Y scan type.

The A/D converter circuit 51 receives analog luminance signals i produced corresponding to respective pixels from the light receiving unit 42 including the CCD image sensors 42a and amplifiers 42b, converts them into an 8-bit digital value of 256 tones and sends it to the pattern side level converter circuit 52a and the contaminant side level converter circuit 52b.

Each of the pattern side level converter circuit 52a and the contaminant side level converter circuit 52b converts a level of the data supplied from the A/D converter circuit 51 into one of 8 levels each of 3 bits to produce a 3-bit data indicative of a multi-valued level which corresponds to the level of the luminance signal. In this embodiment, the pattern side level converter circuit 52a differs from the contaminant side level converter circuit 52b in the range each level for the luminance signal.

The line memory 53 receives multi-valued data of 8 tones each of 3 bits from the pattern side conversion circuit 52a, buffers the 3-bit data, each level of which is converted for respective pixels, for example, 55 pixels corresponding to an area covering 11×5 pixels, namely, the area W having 11 rows and 5 columns as shown in FIG. 2, and sends the 3-bit data corresponding to 55 pixels in parallel to the maximum value detecting circuit 54.

The line memory 53 includes shift registers arranged in a matrix of 3 rows×55 columns which receive 3-bit data on 55 pixels in the area W. Outputs of the 3 rows each including 55 shift registers are sent to the maximum value detecting circuit 54. The shift registers of each row receive, bit by bit, in parallel, 3-bit data which are level-converted by the pattern side level conversion circuit 52a and are shifted by 1-bit every reception of the 3-bit data. Therefore, the oldest level converted data is removed from the shift registers so that a newest data corresponding to a predetermined amount of pixels, in this example, 55 pixels in the area W, is always stored and sent to the maximum value detecting circuit 54.

Alternatively, the line memory 53 may be constructed with a FIFO memory capable of storing data corresponding to 55 pixels in the area W. In such case, an output data of the pattern side level conversion circuit 52a is stored in the FIFO memory sequentially at a predetermined timing and the data stored in the FIFO memory is sent to a register having capacity corresponding to 55 pixels each of 3 bits and provided in the maximum value detecting circuit 54.

The maximum value detecting circuit 54 includes a number of large value detecting circuits 540 for detecting large values and is adapted to determine a data having the maximum value from the multi-valued data corresponding to 55 pixels and send it to the delay circuit 55 and the contaminant judging circuit 57.

Each of the large value detecting circuits 540 comprises a comparator 54a for digitally comparing level-converted 3-bit data of a pixel A with level-converted 3-bit data of a pixel B and a latch circuit 54b for latching one of the level-converted data of the pixels A and B which is larger than the other. The large value detecting circuits 540 are cascade-connected hierarchically to detect the maximum value of the levels of 55 pixels each of 3 bits. That is, large values are detected in a certain hierarchy. The detected large values are compared in a next higher hierarchy to detect a larger value and, in a last state, the maximum value of level is obtained in the latch circuit 54b of the last large value detecting circuit 540.

The 1 chip-Θ delay circuit 55 receives a 3-bit data indicative of one of 8 tones from the contaminant side conversion circuit 52b. Using a pixel Ra at a center of an area W of 11×5 pixels of the maximum value detecting circuit 54 as a reference (cf. FIG. 2), the 3-bit data received by the 1 chip-Θ delay circuit 55 becomes a level-converted value of a luminance signal of a detection pixel S which is separated from the pixel Ra by a distance corresponding to pixels corresponding to 1 chip-Θ, that is, pixels corresponding to one chip minus pixels determined by the inclination angle Θ with respect to the X axis of the wafer 1. The 1 chip-Θ delay circuit 55 produces a 3-bit data delayed from the pixel Ra by 1 chip-Θ, by producing a data delayed by a time corresponding to 1 chip-Θ (predetermined time) corresponding to a sampling time necessary to sample 5000×5-L1 pixels, 1 chip including 5000×5 pixels, as shown by the detection pixel S at a center of the area in FIG. 2. This becomes a data of multi-valued level of the detection pixel S. The contaminant judging circuit 57 receives a data of the detection pixel S whose level is converted into the multi-valued level.

As mentioned, the maximum value in the area W including 11×5 pixels is detected for the reason described below. That is, in theory, it is enough to compare a converted level of a luminance signal of a detection pixel of one chip to be inspected with that of a pixel of an adjacent chip which is in a position corresponding to that of the detection pixel of the one chip. However, the positioning of an optical detection system is not so precise practically. Therefore, the area W is set while a positioning error on the reference side with respect to the contaminant side is taken into consideration and the converted level of the corresponding position is obtained by detecting the maximum value within the area W. Therefore, the size of the area W is not limited to 11×5 pixels and should be determined according to the accuracy of the detecting position, etc., of the optical detection system of the inspection apparatus.

The 2 chip-Θ delay circuit 56 differs from the 1 chip-Θ delay circuit 55 in that the 2 chip-Θ delay circuit has a delay time corresponding to 2 chips-Θ and delays data by a time corresponding to, for example, 2×5000×5 L2 pixels. The 2 chips-Θ delay circuit 56 delays the 3-bit data output from the maximum value detection circuit 54 by a time corresponding to 2 chips-Θ and sends the delayed 3-bit data to the contaminant judging circuit 57. This circuit is adapted to output a level conversion value of a luminance signal of a pixel which has a maximum value of a data of an area W containing a pixel Rb which is a reference pixel delayed from the area W containing the pixel Ra by a time corresponding to 2 chips, as shown in FIG. 2. For simplicity of description, it is assumed here that the pixel Rb at a center position of the area has the maximum value, corresponding to the pixel Ra. Even when the wafer 1 is tilted by the angle Θ, the positions of the pixels Ra and Rb are made correspondent to those shifted from the position of the detection pixel S by one chip in opposite directions, respectively, by calculating delay times by subtracting times corresponding to L1 pixels and L2 pixels from the corresponding pixel positions of the adjacent chips prior to the tilting of the wafer and setting the delay times in the respective delay circuits.

Incidentally, in this example, the wafer 1 is tilted clockwise by the angle Θ with respect to the X axis. However, when the wafer 1 is tilted counterclockwise by the angle Θ, the above mentioned calculating operations in the delay circuits 55 and 56 may be additions of times corresponding to L1 pixels and L2 pixels.

The contaminant judging circuit 57 receives, from the maximum value detection circuit 54, a level conversion data of a pixel having the maximum value in the area W of 11×5 pixels, which is the 3-bit data of the reference pixel Ra, as mentioned previously.

The contaminant judging circuit 57 is constructed with a digital comparator. Assuming that the pixel S is to be inspected, the comparator receives level converted 3-bit data of the reference pixel Ra 1 chip after the pixel S and the reference pixel Rb 1 chip before the pixel S.

The contaminant judging circuit 57 compares the converted level value of the luminance signal of the reference pixel Ra with that of the reference signal Rb to select one of them which is larger. Then, the contaminant judging circuit compares the converted level value of the selected reference pixel with the level converted 3-bit data of the detection pixel S separated from the selected reference pixel by a distance corresponding to 1 chip and, when the data value of the detection pixel S is larger than the comparison data value, produces a detection signal indicative of the existence of contaminant. The contaminant judging circuit 57 produces a contaminant data from the detection and a detection position data composed of X coordinates and Y coordinates and sends the data to the buffer memory 61. At this time, the contaminant judging circuit 57 updates the address of the buffer memory 61 every time the contaminant data is sent and stores the contaminant data in the updated address of the buffer memory 61 sequentially.

The X and Y coordinates mentioned above are sent from the control circuit 25 or the MPU 63 to the contaminant detection unit 50.

The pattern side converter circuit 52a and the contaminant side converter circuit 52b are constructed with RAM's, respectively, which receive the A/D conversion data from the A/D converter 51 and are accessed with the digital value of the detected luminance signal as the address, the data read out from the accessed address being the level-converted value. In this manner, a level-converted data of one of 8 tones each of 3 bits, corresponding to the level of the luminance signal is obtained.

By this conversion, the value of each of the respective luminance signals on the contaminant side is made one of 8 tones S0~S7 and the value of each of the respective luminance signals on the pattern side is made one of 8 tones P0~P7. In the multi-valued level conversion of the luminance signal, the widths of the respective conversion stages of the contaminant side conversion circuit 52b are larger than the widths of the respective conversion stages of the pattern side conversion circuit 52a, so that the luminance signal on the contaminant side, that is, the detection signal, is compressed and level-converted.

Figure 3:
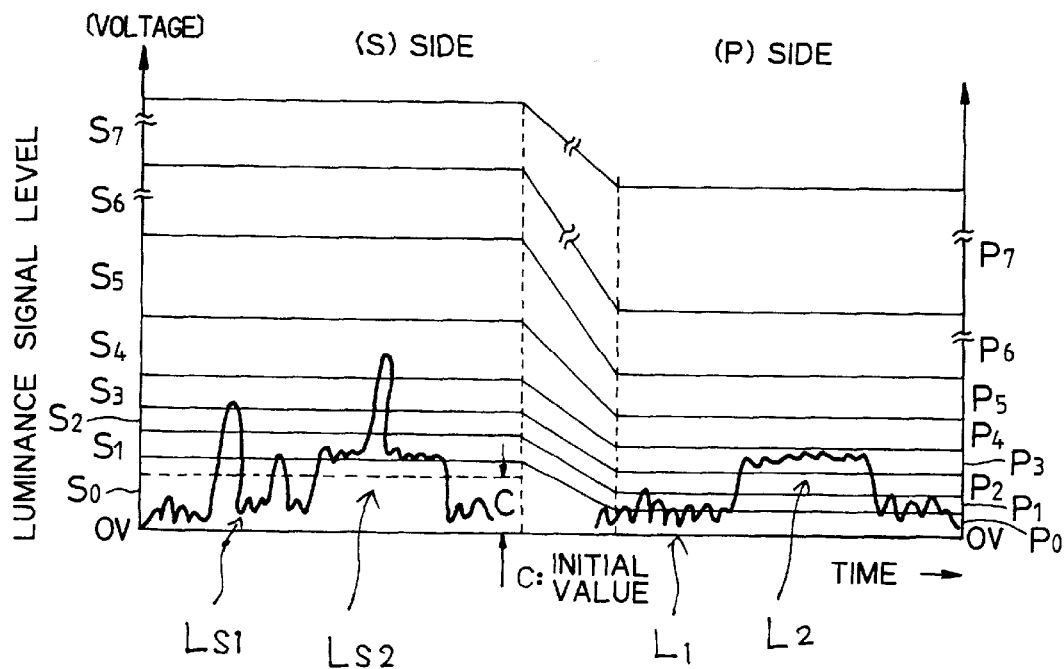
FIG. 3 is a graph explaining a multi-valued level conversion.

The controller 58 has the data stored in the RAM's as a data conversion table. The controller 58 references this table and stores the values of the respective luminance signals as the address values of the RAM's, for example, it stores the converted levels "0" to "7" each of 3-bit data as P0 to P7, as shown in FIG. 3. That is, under the control of the controller 58, the RAM of the pattern side conversion circuit 52a stores "0" in its addresses 0 and 1 as P0, "1" in its addresses 2 and 3 as P1, "2" in its addresses 4 and 5 as P2, "3" in its addresses 6 and 7 as P3, "4" in its addresses 8 to 15 as P4, "5" in its addresses 16 to 23 as P5, "6" in its addresses 24 to 39 as P6 and "7" in its addresses 40 to 64 as P7.

Similarly, under the control of the controller 58, the RAM of the contaminant side conversion circuit 52b stores "0" in its addresses 0 to 7 as S0, "1" in its addresses 8 to 15 as S1, "2" in its addresses 16 to 23 as S2, "3" in its addresses 24 to 31 as S3, "4" in its addresses 32 to 63 as S4, "5" in its addresses 64 to 95 as S5, "6" in its addresses 96 to 159 as S6 and "7" in its addresses 160 to 255 as S7. It is preferable to add an initial value C to the lowest level in the level conversion on the contaminant side as an offset. In the latter case, the last address in the level range of each luminance signal is shifted by adding the value C thereto.

The multi-valued level conversion having steps durations of which are different will be described with reference to FIG. 3.

As mentioned previously, when light receiving condition of a light receiving element is varied or optical detecting condition is varied or changed, the detection level of the same pattern is varied and detection error is produced. However, since adjacent chips of the same wafer are influenced similarly by the light receiving condition and the detecting condition, the influence of the variation of the light receiving condition and/or detecting condition can be restricted relatively by comparing a level of luminance signal from one of these chips with that of another chip as a reference. Further, by converting the luminance signal level into a plurality steps, there is substantially no relative variation of the conversion values as the reference of comparison since the luminance signal from the chip on the contaminant detection side and the luminance signal from the adjacent chip as the reference of comparison are varied similarly.

Since, according to this fact, a pattern area of one chip is compared with a pattern area of the other chip and an area of the one chip which includes no pattern is compared with an area of the other chip which includes no pattern, it becomes unnecessary to distinguish the pattern area from the non-pattern area. However, even in such case, the luminance signal level on the reference side is lowered when the same positions on mutually adjacent chips are compared. On the other hand, when the luminance signal level of the pattern portion on the detection side becomes larger, there may be a case where the luminance signal level on the detection side exceeds the luminance signal level of the reference side. In such case, there is an erroneous detection of contaminant.

According to experiments conducted on a number of wafers, it has been found that a peak level of a luminance signal from contaminant on a pattern area or a non-pattern area is higher than about four times, in average, that from a pattern area or a non-pattern area which has no contaminant. The peak level value may be lowered when a detection level of a luminance signal is low or increased when the accuracy of the optical detection system is improved.

By detecting contaminant using a luminance signal having detection level as high as four times that of the other as a reference according to the experiments, contaminant can be detected even by compressing the luminance signal on the contaminant detection side to one fourth and by comparing it with the luminance signal on the reference side.

That is, since the luminance signal level from contaminant on a pattern is higher than four times in average that from a pattern having no contaminant, even if the luminance signal level is compressed one fourth and converted by the contaminant detection side level conversion circuit 52b, the converted level exceeds the level of the luminance signal from the adjacent chip, which is converted by the pattern side level conversion circuit 52a. Therefore, the detection of contaminant using the high level luminance signal as the reference is possible.

By compressing the detection side luminance signal in this manner, it is possible to lower the converted level of the luminance signal from the pattern portion on the detection side, on which there is no contaminant. Excluding the pixels whose luminance level from the patterned portion is high, it is possible to restrict the converted level value of the patterned portion of the detection side below this level even when the converted level of the pattern on the side of the reference is low. Therefore, it is possible to restricted the erroneous detection of the contaminant.

For this reason, the detection level of the luminance signal is compressed to ¼, in this embodiment. In order to do so, the width of level conversion on the contaminant detection side is made 4 times. FIG. 3 shows the multi-valued level conversion of this kind. A luminance signal L1 is that obtained from an area having no pattern. A luminance signal L2 is that obtained from a pattern area and luminance signals LS1 and LS2 are those obtained from a non-pattern area containing contaminant and a pattern area containing contaminant, respectively.

In FIG. 3, one fourth of, for example, 256 tones each of 8 bits, that is, 64 tones, are assigned to a range of level of the luminance signal on the pattern (P) side having no contaminant and the range is divided to 8 steps, that is, P7=40 to 64, P6=24 to less than 40, P5=16 to less than 24, P4=8 to less than 16, P3=6 to less than 8, P2=4 to less than 6, P1=2 to less than 4 and P0=0 to less than 2.

On the other hand, the 8-level conversion on the contaminant (S) side is performed according to S7~S0=n×P7~P0 where n=4, that is, S7=4×P7=160 to 255, S6=4×P6=96×160, S5=60 to less than 96, S4=38 to less than 16, S3=24 to less than 32, S2=16 to less than 24, S1=8 to less than 16 and S0=0 to less than 8.

The respective data stored in the RAM'S for level conversion correspond to the values mentioned above.

When the contaminant (S) side conversion levels are obtained from the pattern (P) side conversion level, the compression rate n is not limited to 4 and the compression rate may be any so long as, in the S side level conversion, the luminance signal level is reduced to an extent that a pattern is not erroneously detected as contaminant. Particularly, when contaminant is to be detected from a low level luminance signal, n may be set to a value larger than 1 and equal to or smaller than 4.

In general, the width of each step of the multi-valued level conversion of the luminance signal performed by the contaminant side level conversion circuit 52b is m times that of the multi-valued conversion performed by the pattern side level conversion circuit 52a where n is a ratio of a mean value of luminance signal containing contaminant information to a mean value of luminance signal containing no contaminant information and satisfies a relation 1<m<n.

Data for compressing the luminance level may be obtained according to experiments. When the width of the level conversion step is to be obtained as experimental value, an equation S=P+k+C is employed where k is increased with stepping up of the level. It may be possible to set P0 in a range 0~less than k+C and shift the range of each step by adding the initial value C thereto.

The data obtained by using such equation is stored in the data conversion table of the controller 58. The data in the table is set in an internal memory of the controller 58 as data under the control of the micro processor (MPU) 63 of the data processing unit 6. Thus, it becomes possible to arbitrarily set the data value externally under the control of the micro processor 63.

The luminance signal is multi-valued through the 8 steps shown in FIG. 3 and its value is converted into one of 8 tones and compared by the contaminant judging circuit 57. Although the reference of comparison is the maximum value in a given area, it may be the data of the pixels Ra and Rb whose positions correspond to the position of the detection pixel.

In the described embodiment, the luminance signal from a test region on a test chip and the luminance signals from regions of chips adjacent to the test chip are obtained by delaying one and the same luminance signal. In this case, the 1-chip delay circuit 55 may be connected between the A/D converter 51 and the contaminant side level conversion circuit 52a so that the contaminant side level conversion circuit 52b and the pattern side level conversion circuit 52a receive the luminance signal from the contaminant inspection region and the luminance signal from the adjacent chip, respectively. Alternatively, it may be possible to provide the 1−Θ chip delay circuit 55 on the output side of the maximum value detection circuit 54 so that it is connected in parallel to the 2−Θ chip delay circuit 56.

Further, although, in this embodiment, the 1 chip−Θ delay circuit and the 2 chips−Θ delay circuit are provided, the delay times are not limited to 1 chip−Θ' and 2 chips−Θ, so long as the detection signals of corresponding pixel positions of the adjacent chips are obtainable. Further, although these delay times are fixed, respectively, it may be possible to dynamically set delay times in the delay circuits by dynamically detecting the tilting angle Θ of the wafer and calculating the delay times correspondingly to the tilting angle Θ of the wafer on the basis of data supplied from the controller or the MPU correspondingly to the calculated delay times.

What is claimed is:

1. An extraneous substance inspection apparatus for a patterned wafer, which detects extraneous substances on a patterned wafer having patterns in the form of IC chips on a basis of a detection signal which is obtained by irradiating said patterned wafer with a laser beam at a predetermined angle with respect to a surface of said patterned wafer to X-Y scan said wafer and receiving scattering light reflected from said patterned wafer, the detection signal having a magnitude corresponding to a level of the received scattering light, the extraneous substance inspection apparatus comprising: an optical sensor having a plurality of detecting portions respectively arranged to receive the scattering light corresponding to pixels and produce the detection signal corresponding to said respective pixels; a delay circuit responsive to the detection signal from said optical sensor for delaying the detection signal by a predetermined time; and a judging circuit for judging an absence or presence of contaminants by comparing an output of said delay circuit with the detection signal from said optical sensor, wherein said wafer is inclined by a predetermined angle with respect to a direction parallel to the arranging direction of said detecting portions of said optical sensor and the predetermined time corresponds to a difference in scan time between a position of one pixel in a certain chip and substantially the same position as that of the one pixel of another pixel in a chip adjacent to said certain chip, the another pixel being determined corresponding to the predetermined angle in the X-Y scanning.

2. An extraneous substance inspection apparatus for a patterned wafer according to claim 1, further comprising an A/D conversion circuit and wherein said optical sensor comprises a CCD sensor, said detecting portion of said CCD sensor comprises a plurality of detection elements arranged in a line corresponding to respective said pixels, the detection signal is a digital value obtain by A-D converting a signal detected by said CCD sensor by said A/D conversion circuit and said judging circuit compares the digital value with the detection signal.

3. An extraneous substance inspection apparatus for patterned wafer according to claim 2, further comprising a level conversion circuit for converting a level of the detection signal obtained from said one pixel through said optical sensor into one of multi-valued levels, and wherein said delay circuit delays the level-converted detection signal obtained by said level conversion circuit and supplies the delayed signal to said judging circuit and said judging circuit judges a presence or absence of contaminant by comparing the level of the output signal of said delay circuit with the level-converted detection signal obtained by level conversion of the detection signal from a pixel position of another chip adjacent to said certain chip, said pixel position being similar to a position of said one pixel in said certain chip, by said level conversion circuit.

4. An extraneous substance inspection apparatus according to claim 3, wherein the pixel position of said another chip is within a predetermined region and the another signal has a maximum value selected from said predetermined region.

5. An extraneous substance inspection apparatus according to claim 4, wherein said multi-valued levels are three or more, said level conversion means includes first and second level conversion circuits having inputs supplied with the detection signal, widths of the respective steps of the multi-valued conversion of said first level conversion circuit for the detecting signal are larger than widths of the respective steps of the multi-valued conversion of said second level conversion circuit, respectively, an output of said first level conversion circuit is assigned to the signal indicative of the one of multi-valued levels and an output of said second level conversion circuit is assigned to the another signal indicative of a converted level obtained by converting the detection signal detected at the pixel position in said another chip.

6. An extraneous substance inspection apparatus according to claim 5, wherein said delay circuit has a delay time determined on the basis of a time corresponding to one chip and a time determined corresponding to the predetermined angle, said first and second level conversion circuits receive the detection signal of said certain chip and obtain the signal indicative of the converted level of said another chip by delaying an output of said second level conversion circuit by said delay circuit.

7. An extraneous substance inspection apparatus according to claim 6, further comprising a maximum value detection circuit adapted to receive a predetermined number of data and output a data among them which has the maximum value, wherein the output of said second level conversion circuit is sent to said maximum value detection circuit, the output of said maximum value detection circuit being the another signal indicative of the converted level obtained by converting the detection signal detected at the pixel position in said another chip.

8. An extraneous substance inspection apparatus according to claim 5, wherein the width of each step of the multi-valued level conversion of said first level conversion circuit is m times that of the multi-valued conversion of said second level conversion circuit where m satisfies a relation $1<m<n$, where n is a ratio of a mean value of luminance signal containing contaminant information to a mean value of luminance signal containing no contaminant information.

9. An extraneous substance inspection apparatus according to claim 4, further comprising an optical sensor including detecting elements arranged in lines corresponding to a plurality of pixels and adapted to receive the scattering light from said respective pixels and output the detection signal, a buffer memory, a maximum value detection circuit and a delay circuit, wherein the detection signal is a digitized first data, said first level conversion circuit level-converts the first data to obtain a second data, said second level conversion circuit level-converts the first data to obtain a third data, said memory buffer responds to the second data to store a predetermined amount of data by removing an oldest data, said maximum value detection circuit detects one of data stored in said buffer memory which has the maximum value and outputs it as a fourth data, said delay circuit delays one of the fourth data and the third data by a scanning time corresponding to one chip, said judging circuit compares the one data delayed by said delay circuit with the other data not delayed by said delay circuit and judges an existence of extraneous substance when a value of the third data exceeds a value of the fourth data.

* * * * *